United States Patent [19]
Arenberg

[11] Patent Number: 5,501,706
[45] Date of Patent: Mar. 26, 1996

[54] MEDICAL IMPLANT STRUCTURE AND METHOD FOR USING THE SAME

[75] Inventor: Irving K. Arenberg, Englewood, Colo.

[73] Assignee: Wildflower Communications, Inc., Englewood, Colo.

[21] Appl. No.: 346,012

[22] Filed: Nov. 29, 1994

[51] Int. Cl.$^6$ ......................................................... A61F 2/28
[52] U.S. Cl. ............................ 623/16; 623/11; 433/201.1
[58] Field of Search ..................... 623/11, 16; 433/201.1; 523/115, 116; 424/422, 423

[56] References Cited

U.S. PATENT DOCUMENTS

| | | | |
|---|---|---|---|
| 4,321,042 | 3/1982 | Scheicher | 433/201.1 |
| 4,755,184 | 7/1988 | Silverberg | 433/201.1 |
| 4,874,368 | 10/1989 | Miller et al. | |
| 5,002,583 | 3/1991 | Pitara et al. | 623/16 |
| 5,292,253 | 3/1994 | Levy | 433/215 |
| 5,318,779 | 6/1994 | Hakamatsuka et al. | 424/422 |

OTHER PUBLICATIONS

Byrd, et al., "Augmentation of Craniofacial Skeleton with Porous Hydroxyapatite Granules", *Plastic and Reconstructive Surgery*, 91 (1):15–22 (1993).

Goldenberg, R. A., "Hydroxylapatite ossicular replacement prostheses: A four–year experience" *Operative Techniques in Otolaryngology–Head Neck Surgery*, (106) 3: 261–269 (Mar. 1992).

Stein, M. D., et al., "Collagen Sponge as a Topical Hemostatic Agent in Mucogingival Surgery", *J. Periodontal.*, 56 (1):35–38 (Jan. 1985).

Coln, D., et al., "Evaluation of Hemostatic Agents in Experimental Splenic Lacerations", *American Journal of Surgery*, 145: 256–259 (Feb. 1983).

Byrd, H. S., et al., "Augmentation of Craniofacial Skeleton with Porous Hydroxyapatite Granules", *Plastic and Reconstructive Surgery*, 91 (1):23–26 (Jan. 1993).

Kamerer, D. B., et al., "Hydroxyapatite Cement: A New Method for Achieving Watertight Closure in Transtemporal Surgery", *The American Journal of Otology*, 15(1):47–49 (Jan. 1994).

Costantino, P. D., et al., "Hydroxyapatite Cement, I. Basic Chemistry and Histologic Properties", *Arch. Otolaryngol. Head Neck Surg.*, 117:379–384 (Apr. 1991).

Information Summary by Smith & Nephew Richards Company involving collagen foam hydroxyapatite mateials (1993).

"Break a Leg—and Bioceramics May Mend It", *Business Week*, pp. 76–77 (Sep. 12, 1994).

*Primary Examiner*—Paul B. Prebilic
*Attorney, Agent, or Firm*—Klaas, Law, O'Meara & Malkin

[57] ABSTRACT

A medical implant structure and method for making the structure. The implant structure includes a containment member preferably manufactured from collagen (particularly collagen foam) having an open top portion. A supply of a granular implant composition (e.g. hydroxyapatite, natural bone, or bioceramic materials) is positioned within the containment member through the top portion. An activator material (adhesive materials, water, or saline solution) is then added which causes the implant composition to solidify, thereby imparting rigidity to the apparatus. At least one elongate reinforcement member may be positioned within the implant composition during the production process. A cap member may also be placed on the top portion of the containment member. In use, the implant structure is inserted within a patient and positioned adjacent to and against the tissue region to be reinforced. It is then physically shaped to conform with adjacent tissue materials.

23 Claims, 5 Drawing Sheets

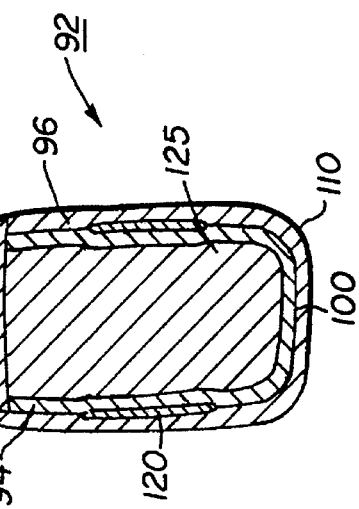
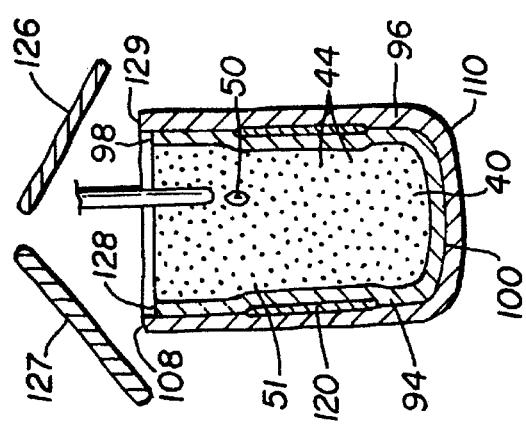
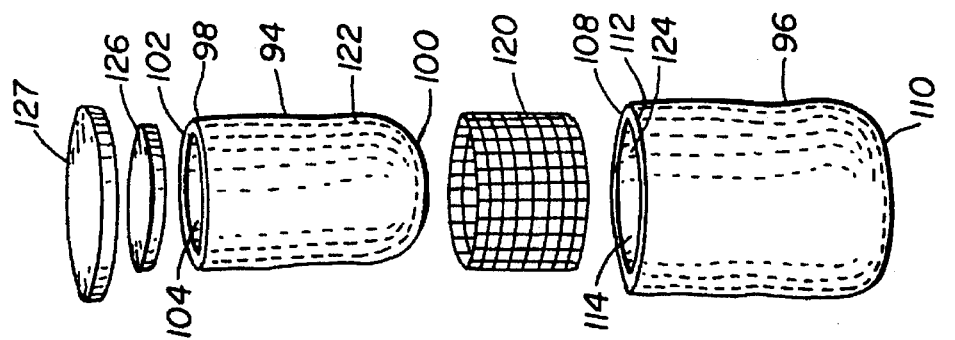

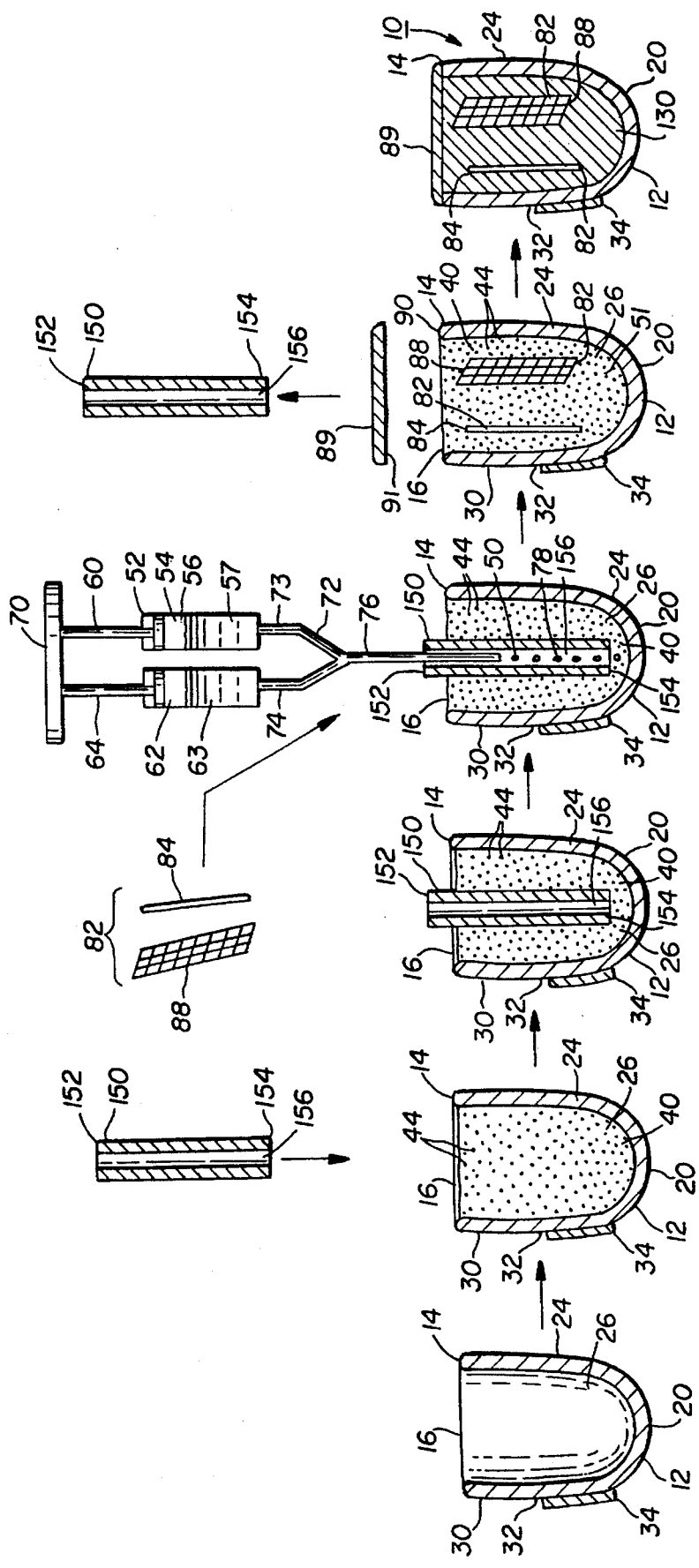

ically to a medical implant structure which may be configured in a variety of shapes/contours for use in various physiological environments, including graft sites and tissue reconstruction zones.

MEDICAL IMPLANT STRUCTURE AND METHOD FOR USING THE SAME

BACKGROUND OF THE INVENTION

The present invention generally relates to medical implant structures for reconstructive and/or constructive purposes, and more particularly to a medical implant structure which may be configured in a variety of shapes/contours for use in various physiological environments, including graft sites and tissue reconstruction zones.

Modern surgical procedures often require the implantation of support structures in various tissue regions to fill gaps, re-contour junction areas between adjacent tissue zones, and otherwise correct structural defects. For example, implant structures may provide numerous benefits in otological procedures (e.g. procedures involving the human ear). Exemplary otological and related procedures which are suitable for the implantation of selected support structures produced in accordance with the present invention include but are not limited to (1) ear canal wall reconstruction; (2) correction of bony posterior fossa/tegmen defects; (3) obliteration of cavities formed during mastoidectomy procedures; (4) correction of bony defects involving the vestibular/cochlear labyrinth; (5) mastoid reconstruction; and (6) reconstruction/obliteration of the eustachian tube or middle ear cleft.

The surgical implantation of tissue support structures as described herein is also important in various procedures involving the skull and related bony elements including the general reconstruction of defective bone/muscle soft tissue regions associated with the anterior skull base, middle cranial fossa skull base, or the posterior cranial fossa skull base. Likewise, the use of reconstructive/constructive implant materials is generally important in connection with cranial vault (skull) defects and/or cranioplasty procedures that create openings or gaps which must be filled.

Other medical/surgical procedures which are appropriate for the implantation of support, space-filling, or recontouring structures produced in accordance with the invention include but are not limited to frontal sinus obliteration, cosmetic surgery, facial plastic reconstructive surgery, chin augmentation, nasal surgery/rhinoplasty, nasal septal reconstruction, and the like. Accordingly, the materials and methods of the present invention as described below shall not be limited to any particular surgical fields, medical uses, or physiological environments.

Prior to development of the present invention, a significant amount of research was conducted regarding surgical reconstructive technology as discussed, for example, in Byrd, et al., "Augmentation of Craniofacial Skeleton with Porous Hydroxyapatite Granules", *Plastic Reconstructive Surgery*, 91:15–22(1993); and Goldenberg, R. A., "Reconstruction of the Middle Ear using Hydroxyapatite Hybrid Prothesis", *Operative Techniques in Otolaryngology-Head and Neck Surgery*, 3(4):225–231 (Dec. 1992). However, a significant need remains for a medical implant structure which offers a substantial degree of structural support and space-filling capacity, is capable of direct physical/biological integration into adjacent tissue materials, and is capable of selective shape adjustment during implantation in order to recontour tissue zones. In particular, a need remains for an implant structure which is capable of direct and immediate shape adjustment by the treating physician during a surgical procedure to facilitate use of the structure for many different purposes. The present invention satisfies these goals and provides numerous other advantages as described in detail below.

SUMMARY OF THE INVENTION

It is an object of the present invention to provide a unique and highly efficient medical implant structure which may be used in a wide variety of physiological environments.

It is another object of the invention to provide a medical implant structure which is readily manufactured using a minimal number of components and process steps.

It is another object of the invention to provide a medical implant structure which is manufactured from biocompatible materials.

It is a further object of the invention to provide a medical implant structure which may be configured in numerous shapes by the treating physician during a surgical procedure.

It is a further object of the invention to provide a medical implant structure which provides substantial space-filling and recontouring capabilities when positioned within a gap or open zone in a selected tissue region.

It is a still further object of the invention to provide a medical implant structure which, after shape adjustment by the treating physician, will retain its shape and thereafter harden to produce a structure of considerable strength and rigidity.

It is an even further object of the invention to provide a medical implant structure which uses a granular implant composition in combination with an activator material (e.g. an adhesive, saline solution, water or other materials) to achieve the objects listed above.

It is an even further object of the invention to provide a medical implant structure which uses a containment member comprised of collagen (e.g. collagen foam or other forms of collagen) in order to form a connective matrix with adjacent tissue materials.

In accordance with the present invention, a medical implant structure is provided which is suitable for use in many different physiological environments. The implant structure described herein may be configured in various shapes by the treating physician during a medical procedure. As a result, precise conformity between the implant structure and adjacent tissue materials is achieved. Once the implant structure is placed in a desired location/position and thereafter activated in accordance with the procedures described below, it rapidly hardens to form a rigid unit. The completed unit is capable of providing an appropriate degree of structural support which may vary, depending on the specific materials and methods used to produce the implant structure, as well as the thickness, width, length, and density (e.g. porosity) of the completed structure.

In a preferred embodiment of the invention, a medical implant structure is provided which includes a containment member having an open top portion, a closed bottom portion, a continuous side wall (which includes an exterior surface), and an internal cavity surrounded by the side wall. The present invention shall not be limited to any particular size, shape, or configuration regarding the containment member and internal cavity. In a preferred embodiment, the containment member is manufactured from collagen. Collagen specifically consists of the fibrous albuminoid constituent of bone, cartilage, and connective tissue. Numerous types of collagen may be used for this purpose, including commercially available collagen materials in various forms. In particular, sheet materials consisting of multi-cellular collagen foam are preferred because they are light in weight, flexible, readily shaped, and will biologically integrate with adjacent tissue materials. Collagen foam is commercially available from many sources including but not limited to Smith & Nephews Richards, Inc. of Memphis Tenn. (USA) which markets a collagen foam product under the name OTOFOAM®. This material is a type I, highly purified bovine collagen with very low antigenicity which is non-toxic, hemostatic, and configured in sponge form. As noted above, collagen materials (especially collagen foam) are desirable for use in producing the containment member of the implant structure since they are flexible and capable of forming a secure biological matrix with adjacent tissue materials. As a result, the completed implant structure will be physically and biologically integrated with adjacent tissues, thereby enabling maintenance of the implant structure in a proper orientation. In addition, it should be noted that sheets of non-cellular (e.g. non foam-type) collagen may also be used to produce the containment member.

In manufacturing the containment member, at least one section of the side wall may optionally include a portion of non-stick coating material applied to the exterior surface of the side wall. The non-stick coating material is used on selected sections of the containment member for which adhesion to adjacent tissue materials is not desired. Exemplary non-stick coating materials suitable for this purpose include but are not limited to silicone rubber and polytetrafluoroethylene (e.g. Teflon®) in tape, sheet, or spray form. Further information regarding the use of non-stick coating materials will be described below.

While the foregoing embodiment involves the use of a single containment member, multiple nested containment members may also be employed in an alternative embodiment. Specifically, a primary containment member which is structurally and functionally identical to the basic containment member described above is positioned (nested) within a secondary containment member. The secondary containment member is substantially identical to the primary containment member in shape and design with one exception. As discussed below, the secondary containment member is about 1–10% larger in size and volumetric capacity than the primary containment member so that the primary containment member can fit entirely within the secondary containment member in a nested relationship. Specifically, the dimensions of the secondary containment member and internal cavity therein are larger than the corresponding dimensions of the primary containment member and its internal cavity by the above-listed percentage.

Also provided in the foregoing alternative embodiment is a layer of reinforcement material which is securely positioned between the primary and secondary containment members. In a preferred embodiment, the layer of reinforcement material may involve many different compositions, including but not limited to silicone rubber, polytetrafluoroethylene (e.g. Teflon®), a biocompatible plastic of a type known in the art which is suitable for medical uses, or a selected ferromagnetic or non-ferromagnetic metal (e.g. titanium), with all of these materials being usable in sheet, rod, pin, or mesh form. As discussed in greater detail below, the layer of reinforcement material may be adhesively affixed to the primary containment member, the secondary containment member, or both. Likewise, attachment of the primary and secondary containment members to each other with the layer of reinforcement material therebetween may be accomplished through the use of staples or sutures passed through both of the containment members and/or adhesive compositions applied to at least one of the containment members. The use of a layer of reinforcement material in the foregoing manner provides a substantial degree of additional strength/structural integrity in the final product which may be necessary in high-stress environments. While the present invention shall be described below in connection with the primary embodiment involving a single containment member, all of the parameters, operating characteristics, and techniques listed herein shall be equally applicable to the above-described alternative embodiment involving dual containment members.

A supply of a granular implant composition is thereafter positioned within the internal cavity of the selected containment member through the open top portion so that the internal cavity is substantially filled with the implant composition. In accordance with the present invention, the term "granular implant composition" shall signify any biocompatible material which, when implanted within a living subject will ultimately constitute a solid mass that is structurally compatible with living bone tissue, and will function in a comparable manner with an equal degree of strength and rigidity. The term "granular" or "granules" may likewise encompass a broad spectrum of particle sizes ranging from large crystals to fine powder as discussed below. Many different compositions fall within the foregoing definitions and are suitable for use in the present invention. While the invention shall not be limited to a particular granular implant composition, exemplary materials suitable for this purpose include but are not limited to the following compositions:

1. Natural bone in granular/powder form derived from a human or animal subject. — If this type of material is selected for use, it is preferred that the selected bone materials are derived directly from the patient who will receive the implant structure described herein. Bone materials may be obtained from the ribs or other bone structures within a patient's body. Bone materials may also be obtained from compatible living donors. As a final alterative, bone materials can be derived from cadavers or may be of animal origin, although this alternative is not preferred in view of potential disease transmission problems and/or biocompatibility problems causing rejection of the bone materials by the patient.

2. Synthetic or natural (purified) hydroxyapatite granules. — Hydroxyapatite is the basic composition in human bone and chemically consists of $Ca_{10}(PO_4)_6(OH)_2$. The term "granules" as used herein shall again involve many different particle sizes as discussed below.

3. A granular/powdered commercially-available bioceramic composition consisting primarily of glass and/or ceramic particles manufactured from silicates, calcium phosphates, and other compositions normally used in glass technology.

4. Synthetic or naturally-derived powdered hydroxyapatite cement materials — As discussed in further detail below, this material involves a combination (mixture) of tetracalcium phosphate and dicalcium phosphate anhydrous.

The foregoing materials will be discussed in further detail below, and represent only a selected listing of granular implant compositions which may be used in the present invention. As noted above, the invention shall not be limited to any particular implant compositions, and is prospectively applicable to all commercially-available products determined to be useful in the grafting or reconstruction of bone/tissue materials.

In order to form a solid mass from the granular implant compositions listed above, the desired composition is combined with an activator material. The activator material basically consists of a selected liquid composition which is supplied to the internal cavity of the containment member and combined (mixed) with the granular implant composition. This process causes the implant composition to agglomerate in order to form a soft, pliable mixture (e.g. a paste) which ultimately solidifies into a solid, hardened mass encapsulated by the collagen containment member. The hardened mass enables the completed containment member to be sufficiently rigid for use as an implant structure in a variety of different environments. Numerous activator materials may be employed to produce the solid mass, including but not limited to autologous fibrin glue, silicone rubber cement, cyanoacrylate glue, sterile water, physiological saline solution, as well as various biocompatible adhesive compositions which are known in the art and have been approved by the United States Food and Drug Administration for medical use. The type of activator material to be used will basically depend on the particular granular implant composition selected for use in a given medical application, and the present invention shall not be limited to any particular activator materials. For example, items (1)–(3) listed above (e.g. granular/powdered natural bone, synthetic or natural (purified) hydroxyapatite granules, and/or bioceramic materials) are more appropriately combined with adhesive compositions including but not limited to those listed above (e.g. autologous fibrin glue, silicone rubber cement, cyanoacrylate glue and numerous other commercially available, biologically acceptable adhesive compositions which have been approved by the United States Food and Drug Administration for medical use). These materials (e.g. items (1)–(3) described above) will have a preferred particle size diameter of between about $1/100$–$1/4$ in. In situations involving hydroxyapatite cement (item (4) above) which normally involves a small particle size diameter of about $1/100$ in. or less, water (preferably of a sterile character) or physiological (e.g. 0.9%) NaCl saline solution may be used. The above-listed activator materials shall be described in further detail below in terms of quantity, applicability, and other technical parameters. Also, the selection of any given activator material will be undertaken in accordance with preliminary pilot studies on the implant compositions and physiological environment under consideration.

As described in further detail below, numerous fluid delivery systems including specialized syringes may be employed to supply the activator materials to the granular implant composition in an appropriate amount and at a desired rate. It should also be noted that when adhesive materials are used to activate the implant composition, they may be employed in powder form, followed by the addition of hydrating materials thereto (e.g. water). This alternative procedure shall be deemed equivalent to the processes described above which involve the direct addition of liquid adhesive materials.

In a further alternative embodiment of the invention, delivery of liquid activator materials to the granular implant composition may be undertaken using a tubular (hollow) rod member having a central elongate bore therethrough which is initially inserted within the implant composition in the containment member. The rod member includes open first and second ends which permit uninterrupted communication with the bore. In addition, the rod member is optimally manufactured from an inert, non-reactive material (e.g. silicone rubber, plastic, glass, or metal). After placement of the rod member into the granular implant composition within the containment member, the selected liquid activator material is supplied to the elongate bore using a syringe or other conventional fluid delivery system. Based on the texture, consistency, density, and overall character of the implant composition (as well as the small size of the bore in the rod member which is further discussed below), minimal amounts of the composition will enter upwardly into the bore during insertion of the rod member therethrough. As a result, the bore will remain open in an amount sufficient to receive the liquid activator material therein. After addition of the liquid activator material to the bore in the rod, the activator material will either immediately drain into the granular implant composition or collect within the bore and drain gradually into the composition. Drainage rates associated with the activator material will depend on a variety of factors including the particle size of the granular implant composition being used, as well as the amount of activator material being added. The rod member is then removed from the implant composition. In situations where the liquid activator material has collected within the bore, remaining amounts of the activator material within the bore will drain into and through the implant composition in a continuous, uniform manner from the lower end of the rod member during the removal process. Introduction of the activator material using the foregoing method enables rapid and complete dispersion of the material throughout the granular implant composition, including portions thereof at the bottom of the containment member. As a result, a final implant structure of uniform consistency and integrity is produced.

In a variation of the foregoing procedure, the rod member may be allowed to remain within the implant composition in the containment member after the activator materials have been delivered in order to provide the completed implant structure with additional internal support. If the rod member is to remain within the containment member, it is preferred that it be constructed of a material which is bendable during placement of the implant structure within a patient. An exemplary material suitable for this purpose would involve silicone rubber or a selected biocompatible plastic.

Alternatively, results equivalent to those described above may be achieved when the liquid activator material is added to the elongate bore of the rod member during actual removal of the rod member from the granular implant composition (e.g. as the rod member is being pulled upwardly and out of the containment member). This process is described in further detail below, and is especially useful when the activator material enters the implant composition at a slow rate and large quantities of activator material are involved (e.g. amounts exceeding the volumetric capacity of the bore through the rod member).

To provide additional strength and stability in the completed implant structure, at least one elongate reinforcement member may optionally be positioned/imbedded within the granular implant composition prior to, during, or immediately after addition of the activator material to the selected implant composition. The reinforcement member is preferably constructed of metal, and may consist of one or more elongate rods, pins, portions of mesh, and the like. Exemplary and preferred metals suitable for use as the reinforcement member include but are not limited to titanium and stainless steel. It is also contemplated that other materials may be used to construct the reinforcement member, including biocompatible plastics which are known in the art for medical purposes, polytetrafluoroethylene (e.g. Teflon®), and equivalent materials. A determination as to whether the addition of reinforcement members is necessary will depend on the environment in which the implant structure is used and how much stress it will encounter.

To maintain the granular implant composition, activator material, and any reinforcement members within the containment member during production of the implant structure and after completion, at least one cap member is preferably secured to the open top portion of the containment member. In a preferred embodiment, the cap member is manufactured from the same material used to construct the containment member collagen foam and/or other forms of collagen discussed below). The cap member is preferably secured to the containment member using a selected adhesive composition such as autologous fibrin glue or other conventional biocompatible adhesives.

The final product (e.g. completed implant structure) may be prepared immediately before or during a surgical procedure. It is then positioned in a desired location within a patient adjacent to and against the tissue materials of concern (bony or soft tissues which require support or structural augmentation). It should be noted that the term "patient" and "living subject" as used herein shall encompass both human and animal subjects (both research and veterinary specimens). Proper placement of the implant structure within the selected tissue regions of a patient is undertaken in a timely manner prior to solidification of the granular implant composition. In this regard, the implant structure may be physically molded (configured and shaped) in situ by the treating physician so that it will more precisely conform to the contours of surrounding tissue materials before solidification. The benefits of conformity in this manner will be discussed below.

After surgical insertion and shaping of the implant structure, it will solidify to produce a product with a considerable degree of strength. The support capabilities of the implant structure will depend on the construction materials being used, including the quantity and type of reinforcement members integrated within the containment member. Furthermore, the collagen materials (e.g. collagen foam) used to manufacture the containment member will adhere, conform, and physiologically/biologically integrate into the surrounding tissue regions, thereby providing a highly effective, rigid, and permanently oriented implant structure.

These and other objects, features, and advantages of the present invention shall be provided below in the following Brief Description of the Drawings and Detailed Description of Preferred Embodiments.

BRIEF DESCRIPTION OF THE DRAWINGS

FIGS. 4A–4C involve sequential, partially cross-sectional schematic illustrations of the components and materials used in producing an alternative medial implant structure which incorporates dual containment members.

FIGS. 5A–5F involve sequential, partially cross-sectional schematic illustrations of the components and materials used in producing the medical implant structure of FIGS. 2–3 in accordance with an alternative production method.

DETAILED DESCRIPTION OF PREFERRED EMBODIMENTS

Figure 1:
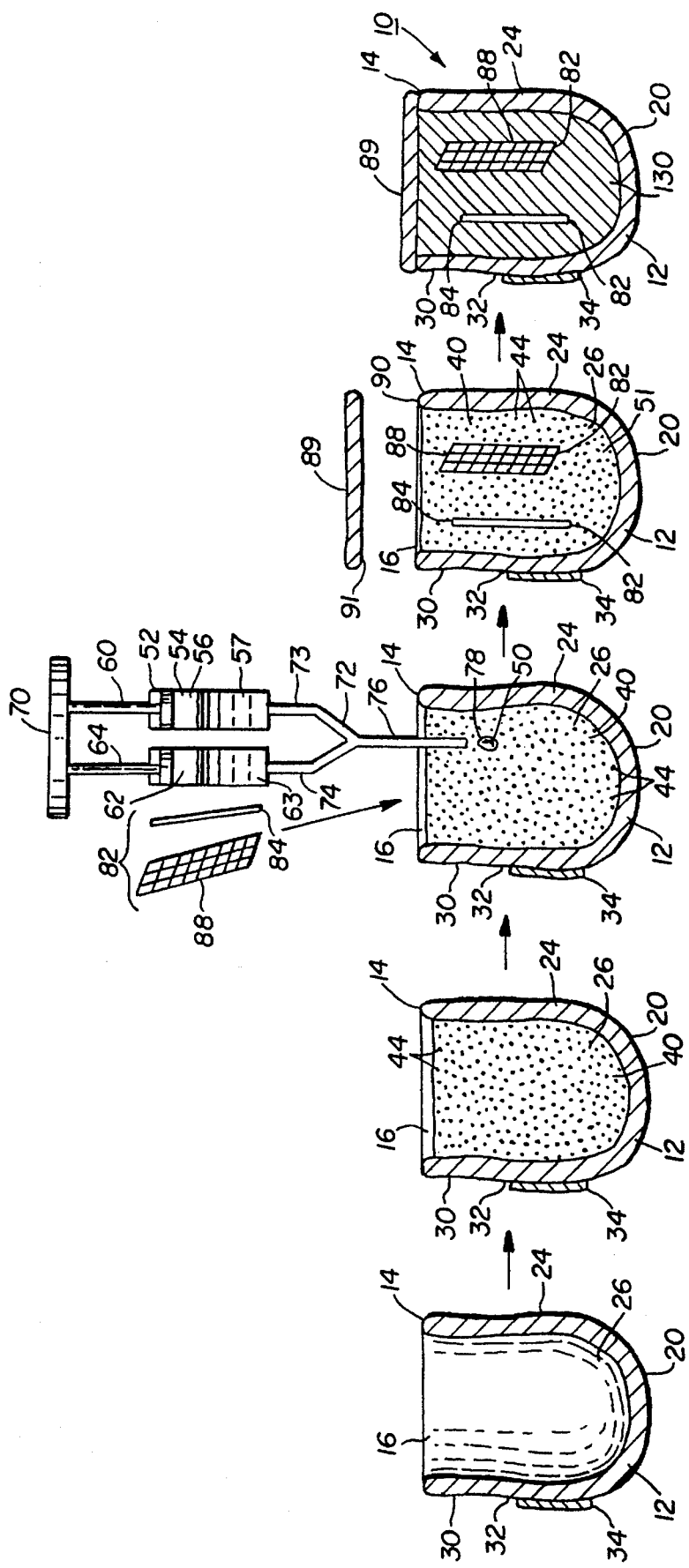
FIGS. 1A–1E involve sequential, partially cross-sectional schematic illustrations of the components and materials used in producing a medical implant structure in accordance with the present invention.

The present invention involves a unique and highly effective medical implant structure which is suitable for use in a wide variety of physiological environments. The implant structure described herein may be used for both constructive and reconstructive purposes in many different surgical procedures. Exemplary uses for the implant structure are listed above. In particular, the implant structure of the present invention offers considerable utility in connection with tissues and components of the human ear. For example, as previously noted, implant structures manufactured in accordance with the invention are especially useful regarding ear canal wall reconstruction, the filling of open zones caused by tumor removal, and bone loss due to osteomyelitis, mastoidectomy and the like. However, the present invention shall not be limited to otological applications or any particular surgical procedures/reconstructive processes. The invention shall also not be restricted to use in connection with any particular tissue materials and is applicable in a wide variety of neurosurgical, otological, dental, orthopedic, and plastic surgery/reconstructive procedures.

An important aspect of the invention involves the pliable, selectively shapable character of the implant structure prior to solidification. This feature enables the implant structure to be physically shaped and manipulated by the treating physician so that it will precisely conform with surrounding tissue regions and materials. As a result, the implant structure will conformingly engage the tissue materials of concern in a precise manner so that interference with adjacent tissue regions, passageways, and organs is avoided. Furthermore, conforming engagement in this manner will enable the implant structure to provide a maximum degree of shape retention, structural support, physical integration, and stability within the patient after solidification of the implant structure.

With reference to FIGS. 1A–1E, 2, and 3, production of an exemplary medical implant structure in accordance with the invention is illustrated. The completed implant structure is generally designated in the drawing figures at reference number 10. It should be noted that the implant structure 10 shall not be limited to any particular size or dimensional parameters. The size and dimensions of the implant structure 10 will necessarily vary based on its intended use. For example, an implant structure used in the ear canal will have a minimal size compared with an implant structure used for reconstructive jaw surgery or skull base defects. While the present invention shall not be limited to any particular size parameters, implant structures may generally be produced having a length ranging from about 0.5–4.0 in. and a width between about 0.5–4.0 in. Implant structures having dimensional configurations outside of these ranges are also possible, depending on the intended environment in which the implant structures are to be used.

With continued reference to FIGS. 1A–1E, production of the implant structure 10 in accordance with a preferred embodiment of the invention is illustrated. As shown in FIG. 1A, a containment member 12 is provided which includes an open top portion 14 having an opening 16 therein and a closed bottom portion 20. In addition, the containment member 12 further includes a continuous tubular side wall 24, and an internal cavity 26 therein surrounded by the side wall 24. In a preferred embodiment, the side wall 24 will have a thickness of about 1/16–1/2 in. In most cases, the internal cavity 26 will have a volume of about 0.10–10 oz., although the ultimate volume of the cavity 26 will vary based on the desired size of the implant structure 10 and its intended use.

The containment member 12 is preferably manufactured (e.g. molded, pressed, or stamped) from sheets of a multi-cellular composition known as "collagen foam". This material is presently available from Smith & Nephew Richards Inc. of Memphis, Tenn. (USA) under the name OTO-FOAM®. Collagen foam is normally manufactured from non-denatured, purified bovine collagen (type I). It is highly hemostatic and promotes the aggregation of blood platelets. It is also characterized by a substantial degree of strength and structural integrity. Collagen foam materials are generally discussed in Stein, M.D., et al., "Collagen Sponge as a Topical Hemostatic Agent in Mucogingival Surgery", *J. Periodontal.*, 56(1):35–38 (Jan. 1985); and Coln, D., et al., "Evaluation of Hemostatic Agents in Experimental Splenic Lacerations", *American Journal of Surgery*, 145:256–259 (Feb. 1983). Additional information regarding the benefits and characteristics of collagen foam when used in connection with the containment member 12 will be described below.

It should also be noted that other types of collagen material may be used in connection with the containment member 12 aside from collagen foam. For example, sheets of solid, non-cellular collagen materials which are suitably formed (e.g. molded), attached, or connected together by adhesives and the like may be used to construct the containment member 12. Non-cellular (non-foam) collagen sheet materials suitable for use in connection with the present invention are commercially available from numerous sources including but not limited to the Collagen Corporation of Palo Alto, Calif. (USA). Accordingly, the present invention shall not be restricted to any particular type of natural or artificial collagen materials used to construct the containment member 12, with the terms "collagen" and "collagen materials" encompassing a wide variety of commercially available natural and artificial forms ranging from foam to solid, non-cellular compositions as noted above. While many different types of collagen may be used, foam materials are nonetheless preferred in view of their flexibility, hemostatic nature, and enhanced ability to physically/biologically integrate with tissue materials as described below. Also, collagen materials are preferred for construction of the containment member 12 because of their durability, strength, and biocompatibility.

As schematically illustrated in FIG. 1A, the exterior surface 30 of the side wall 24 may optionally include at least one section 32 which includes a portion of non-stick coating material 34 applied thereto. While the embodiment of FIG. 1 illustrates only a single section 32 having a non-stick coating material 34 thereon, it is contemplated that the containment member 12 may actually include multiple sections which include non-stick coating materials if desired. In a preferred embodiment, the non-stick coating material 34 will have an optimal thickness of about 1/64–1/8 in., and may consist of a thin sheet of conventional silicone rubber or a portion of self-adhesive tape manufactured from polytetrafluoroethylene (e.g. Teflon®). Other non-stick coating materials may also be used, including commercially available spray compositions which include non-stick materials therein (e.g. spray compositions containing Teflon®). In this regard, the present invention shall not be limited to any particular compositions for this purpose. If the selected non-stick coating material 34 is not self-adhesive, it may be affixed to the exterior surface 30 of the containment member 12 using a conventional adhesive composition. Exemplary compositions suitable for this purpose include but are not limited to commercially available cyanoacrylate adhesives, silicone rubber cement, and other compositions known in the art which are approved for use in medical applications by the United States Food and Drug Administration. The selected adhesive composition may be applied directly to the non-stick coating material 34, to the exterior surface 30 of the side wall 24, or to both of these structures. Even if the non-stick coating material 34 is self-adhesive as in the case of adhesive polytetrafluoroethylene tape, additional adhesives or glue materials may be used as described above to ensure proper affixation of the non-stick coating material 34 to the containment member 12. The non-stick coating material 34 is designed to prevent biological integration and adhesion of the implant structure 10 to adjacent sections of tissue materials under certain circumstances. Further information regarding the use and functional capabilities of the non-stick coating material 34 will be provided below.

With reference to FIG. 1B, the containment member 12 is then filled with a supply of a granular implant composition 40. Specifically, the internal cavity 26 is entirely filled (e.g. up to the open top portion 14) with the implant composition 40 through the opening 16 in the open top portion 14.

In accordance with the present invention, the term "granular implant composition" shall signify any biocompatible material which, when implanted within a living subject, will ultimately constitute a solid mass that is structurally compatible with living bone tissue, and will function in a comparable manner with a substantially equal degree of strength and rigidity. The terms "granular" and "granules" used herein may likewise encompass a broad spectrum of particle sizes as discussed below regarding exemplary implant compositions appropriate for use in the present invention. Many different compositions fall within the foregoing definitions and are suitable for use in the invention. While the invention shall not be limited to a particular granular implant composition, exemplary materials suitable for this purpose include but are not limited to the following compositions:

1. Natural bone in granular/powder form derived from a human or animal subject. — As noted above, if this type of material is selected for use, it is preferred that the bone materials be derived directly from the patient who will receive the implant structure described herein. Bone materials may be obtained from the ribs or other bone structures within the patient's body. Bone materials may also be obtained from compatible living donors. As a final alterative, bone materials can be derived from cadavers or may be of animal origin, although this alternative is not preferred in view of potential disease transmission problems and/or biocompatibility problems causing rejection of the bone materials by the patient. An exemplary and suitable particle size diameter appropriate for use in connection with natural granular/powdered bone materials is about 1/100–1/4 inch.

2. Synthetic or natural (purified) hydroxyapatite granules. — Hydroxyapatite is the basic composition in human bone and chemically consists of $Ca_{10}(PO_4)_6(OH)_2$. The term "granules" as used herein shall again involve many different particle sizes as discussed below. However, typical hydroxyapatite granules suitable for use in the present invention will involve an average particle size diameter of about 1/100–1/4 inches. Further information regarding hydroxyapatite materials in general is provided in "Augmentation of Craniofacial Skeleton with Porous Hydroxyapatite Granules", *Plastic Reconstructive Surgery*, 91:15–22(1993) which is incorporated herein by reference. Such materials are commercially available from Smith & Nephew Richards Inc. of Memphis Tenn. (USA). In addition, a commercial product consisting of hydroxyapatite granules derived from the exoskeletons of sea polyps is available from Interpore International of Irvine, Calif. (USA)

3. A granular or powdered commercially-available bioceramic material consisting primarily of glass and/or ceramic particles manufactured from silicates, calcium phosphates, and other compositions normally used in glass/ceramic technology. — These materials are typically proprietary in nature. However, exemplary commercially-available products falling within this category are sold by U.S. Biomaterials Corporation of Baltimore, Md. (USA) under the trademark Bioglass®. This material consists of an amorphous glass composition, and is further discussed in an article entitled "Break a Leg and Bioceramics May Mend It", *Business Week*, pp. 76–77 (Sep. 12, 1994) which is incorporated herein by reference. Again, such a material may be used in a variety of different particle size diameters, with an optimal range being about $1/100$–$1/4$ in.

4. Synthetic or naturally-derived powdered hydroxyapatite cement — This material involves a combination (mixture) of tetracalcium phosphate and dicalcium phosphate anhydrous, and is discussed in Kamerer, D. B., et al., "Hydroxyapatite Cement: A New Method for Achieving Watertight Closure in Transtemporal Surgery", *The American Journal of Otology*, 15(1):47–49 (Jan. 1994); and Constantino, P. D., et al., "Hydroxyapatite cement, I. Basic Chemistry and Histologic Properties", *Arch. Otolaryngol. Head Neck Surg.*, 117:379–384 (Apr. 1991) which are incorporated herein by reference. Exemplary particle size diameters associated with this composition which are suitable for use in the present invention range from about $1/100$ in. or less (e.g. a fine powder).

The foregoing items represent only a selected list of granular implant compositions which may be used in the present invention. As noted above, the invention shall not be limited to any particular implant composition, and is prospectively applicable to all commercially-available compositions determined to be useful in the grafting or reconstruction of bone/tissue materials. Likewise, the present invention shall not be exclusively limited to any particle size values associated with the granular implant compositions. Specific compositions and particle size parameters will vary in view of numerous factors including but not limited to the size of the implant structure being used, as well as the intended environment associated with the implant structure. Accordingly, specific compositions and particle sizes for any given situation shall be determined in connection with preliminary pilot studies which consider the intended use of the completed implant structure.

The selected granular implant composition 40 is used in an amount sufficient to substantially fill the internal cavity 26 as noted above. Thereafter, as illustrated in FIG. 1C, an activator material 50 is introduced into the internal cavity 26 and combined with the implant composition 40. The activator material 50 causes the individual granules 44 of the implant composition 40 to adhere together to form a pliable mixture 51 (FIG. 1C) which ultimately solidifies to produce a solid mass. The term "pliable" as used herein shall constitute a mixture which is soft, flexible, and selectively shapable by the treating physician. As a result, a rigid implant structure 10 is produced (FIG. 1E).

Many different compositions may be used as the activator material 50, and the present invention shall not be limited to any particular compositions for this purpose. The type of activator material 50 to be selected will basically depend on the particular implant composition 40 being used, the particle size thereof, the desired strength of the completed implant structure, and other factors. For example, larger, more granular materials having a particle size (diameter) of between about $1/100$–$1/4$ in. are more appropriately combined with adhesive compositions including but not limited to those listed above (e.g. autologous fibrin glue, silicone rubber cement, cyanoacrylate glue and numerous other commercially available, biologically acceptable adhesive materials which have been approved by the United States Food and Drug Administration for internal use). In this regard, adhesive materials are more appropriately used in connection with natural granular/powdered bone, synthetic or natural (purified) hydroxyapatite granules, or bioceramic compositions of the types listed above (e.g. items (1)–(3)). Autologous fibrin glue is a preferred composition suitable for use as the activator material 50. This composition is referenced in U.S. Pat. No. 4,874,368 to Miller et al. It specifically involves a combination of two blood components, namely, fibrinogen and thrombin. Because autologous fibrin glue is a natural product, it avoids toxicity problems which may occur when synthetic adhesive materials are used. In this regard, autologous fibrin glue is a highly biocompatible material. In manufacturing autologous fibrin glue, the thrombin portion thereof may be of bovine origin, and is commercially available from many sources including but not limited to ICN Biomedicals, Inc. of Irvine, Calif. (USA). Fibrinogen can be derived from the plasma of the particular patient being treated or may be obtained from compatible donors. In particular, concentrated supplies of plasma from selected patients and/or donors may be used as a suitable source of fibrinogen. Commercial supplies of bovine fibrinogen appropriate for use in the present invention may likewise be obtained from ICN Biomedicals, Inc. of Irvine, Calif. (USA).

In order to use autologous fibrin glue, the foregoing thrombin and fibrinogen components are combined immediately prior to or during use. Combination of these components results in an adhesive/sealant mass which is highly biocompatible as previously noted. To use autologous fibrin glue (or any other suitable liquid adhesive) as the activator material 50, it is delivered using a selected liquid delivery system 52 (FIG. 1C). The delivery system 52 may consist of a single, conventional syringe unit (not shown) or a specialized dual syringe unit 54 which is preferred when autologous fibrin glue is involved. The dual syringe unit 54 is of a type which is commercially available from Micromedics, Inc. of Eagan, Minn. (USA). The dual syringe unit 54 has a first chamber 56 designed to receive a supply of fibrinogen 57 therein. As noted above, the fibrinogen 57 may be of bovine origin or in the form of a blood plasma concentrate from a selected patient or donor. The first chamber 56 has a conventional plunger assembly 60 slidably positioned therein. Also included is a second chamber 62 adapted to receive a supply of thrombin 63 therein. The second chamber 62 has a conventional plunger assembly 64 slidably positioned therein. The plunger assemblies 60, 64 are operatively connected by a single external handle member 70 as schematically illustrated in FIG. 1C.

Connected to the first and second chambers 56, 62 and in fluid communication therewith is a fork-shaped tubular needle 72 having dual upper sections 73, 74 and a single elongate lower section 76 (FIG. 1C). To deliver a completed supply of autologous fibrin glue to and within the granules 44 of implant composition 40 for use as the activator material 50, the handle member 70 of the dual syringe unit 54 is compressed causing simultaneous expulsion of the fibrinogen 57 and thrombin 63 from their respective chambers 56, 62 by plunger assemblies 60, 64. The fibrinogen 57 and thrombin 63 thereafter respectively pass through the upper sections 73, 74 of the needle 72 and combine within the lower section 76. A completed supply of liquid autologous fibrin glue 78 is then expelled into the implant composition 40 (hydroxyapatite granules 44) via the lower section 76 of needle 72.

As noted above, the present invention shall not be limited exclusively to the use of autologous fibrin glue or any particular adhesive materials. For example, additional adhesive compositions suitable for use as the activator material 50 are listed above which are all in liquid form. In addition, the present invention shall not be limited to any specific delivery systems for the selected activator material 50 (e.g. adhesive composition). For example, when autologous fibrin glue is used as the activator material 50, two separate syringe units may be used to respectively deliver thrombin and fibrinogen materials instead of the dual syringe unit 54. Also, a single syringe unit (not shown) of conventional construction and design may be used to deliver other adhesive materials which contain a single active ingredient (e.g. cyanoacrylate adhesives). It should likewise be noted that when adhesive materials are used, they may be employed in powder form, followed by the addition of hydrating materials thereto (e.g. water). This alternative procedure shall be deemed equivalent to the processes described above which involve the direct addition of liquid adhesive materials.

In situations involving hydroxyapatite cement materials (e.g. item (4) above) used as the granular implant composition 40, water (preferably of a sterile character) or physiological (e.g. 0.9% by weight) saline (NaCl) solution may be used as the activator material 50 instead of the adhesive compositions described above. However, the foregoing adhesive materials may nonetheless be used with the hydroxyapatite cement composition if desired, although the water and/or saline solution is preferred. The selection of any given activator material 50 will depend on a wide variety of factors determined by routine preliminary pilot studies. These factors include but are not limited to the character and consistency of the granules 44 associated with the implant composition 40, the intended size of the completed implant structure 10, and the environment in which the implant structure 10 will be used.

While the amount of activator material 50 to be used will necessarily vary in view of the ultimate size of the implant structure 10 and quantity of implant composition 40 therein, it can generally be stated that approximately 0.1–10 ml of the selected liquid activator material 50 will be used for each gram of granular implant composition 40. Within the foregoing range, larger amounts of activator material 50 will typically be used when the individual granules associated with the implant composition are of a small, powder-like size (e.g. about 1/100 in. in diameter or less) due to the increased surface area which must be wetted with the activator material 50. The precise amount and type of activator material 50 to be used may be determined in connection with preliminary pilot tests on the materials of interest. Accordingly, the present invention shall not be restricted to the foregoing numerical values as noted above.

Regardless of the specific amount and type of activator material 50 to be used, it should be supplied in a manner sufficient to contact and wet substantially all of the granules 44 within the containment member 12. To facilitate this goal, it may be necessary when an implant structure 10 of large size is involved to agitate or mix the granules 44 with the selected activator material 50 immediately after delivery of the activator material 50 to the containment member 12. Mixing may be accomplished using the needle of the selected syringe unit used for delivery or any other elongate member suitable for this purpose.

While the foregoing production method is preferred, the activator material 50 and implant composition 40 may also be combined outside of the containment member 12 to form a mixture which is thereafter placed in the containment member 12. This alternative method shall be deemed equivalent to the method described above and illustrated in FIGS. 1A–1E.

With reference to FIGS. 1C–1D, at least one elongate reinforcement member 82 may be inserted (embedded) within the implant composition 40 in the containment member 12 before, during, or immediately after addition of the activator material 50. In a preferred embodiment, the reinforcement member 82 will be positioned within the implant composition 40 prior to addition of the activator material 50 to provide sufficient time for proper orientation and shaping of the reinforcement member 82 within the implant composition 40 in the internal cavity 26 of the containment member 12. However, the present invention shall not be limited regarding the specific point in time when the reinforcement member 82 is inserted, with all of the foregoing alternatives being considered equivalent to each other. The present invention shall also not be restricted to any particular quantity of reinforcement members 82. One or more reinforcement members 82 may be used, depending on the intended use, shape, and configuration of the completed implant structure 10 and how much stress it will encounter. The reinforcement member 82 may involve a number of different structural forms. For example, the reinforcement member 82 may consist of an elongate pin or rod 84, an elongate portion of wire mesh 88, or both. In either form (e.g. rod 84 or mesh 88), it is preferred that the reinforcement member 82 be manufactured of a strong, substantially rigid and inert material which can be selectively bent, shaped or contoured by the treating physician during insertion of the implant structure 10, with the reinforcement member 82 retaining its chosen shape after the physical manipulation thereof. However, the selected construction material should be sufficiently strong so that the reinforcement member 82 will resist bending forces and further deformation after the implant structure 10 is surgically inserted. As a result, the reinforcement member 82 will retain the particular shape chosen by the treating physician. In this regard, use of the reinforcement member 82 within the implant structure 10 will assist in maintaining the selected configuration of the entire structure 10 after surgical insertion. Exemplary construction materials suitable for producing the reinforcement member 82 will consist of titanium, stainless steel, and biocompatible plastic materials known in the art which are conventionally used in medical applications. Titanium is preferred because of its strength and non-ferromagnetic character. Metals which are ferromagnetic are capable of obtaining a high degree of magnetization when exposed to weak magnetic fields. Ferromagnetic metals cannot be used in patients undergoing medical resonance imaging (MRI) procedures. Being nonferromagnetic, titanium will not interfere with current medical diagnostic processes which involve MRI technology. It should also be noted that the relative thickness of the materials used to construct either form of the reinforcement member 82

(e.g. rod 84 or mesh 88) may vary, depending on the intended use of the implant structure 10. However, an exemplary thickness (diameter) range regarding the rod 84 will be about 1/16–1/4 in. With respect to the strand or wire materials used to produce the mesh 88, the preferred thickness (diameter) thereof will be about 1/64–1/8 in., with the average size (e.g. width and length) of each opening in the mesh 88 ranging from about 1/64–1/4 in. Nonetheless, these parameters are provided for example purposes, and the present invention shall not be limited to any particular dimensions associated with the reinforcement member 82.

After combination of the activator material 50 with the granules 44 of implant composition 40, a cap member 89 is attached to the open top portion 14 of the containment member 12 in order to seal the opening 16 therein and retain the pliable mixture 51 within the containment member 12 (FIGS. 1D–1E). In preferred embodiment, the cap member 89 will be constructed (e.g. stamped, punched or molded) from the same materials used to manufacture the containment member 12 including collagen foam or other collagen materials. However, the present invention shall not be limited to any particular materials regarding construction of the cap member 89. The cap member 89 is secured to the rim 90 on the open top portion 14 using a selected adhesive which is applied to the underside 91 of the cap member 89, to the rim 90, or to both of these components. The adhesive may involve a number of different compositions. However, in a preferred embodiment, adhesive compositions suitable for use in attaching the cap member 89 may be the same as those associated with the activator material 50 (e.g. autologous fibrin glue, silicone rubber cement, or cyanoacrylate glue). Use of the cap member 89 ensures that the components within the containment member 12 (the granular implant composition 40, the activator material 50 and/or the reinforcement members 82) do not become displaced during production of the implant structure 10 and after completion of the production process. It should also be noted that the cap member 89 has a preferred thickness which is substantially equal to that of the side wall 24 associated with the containment member 12 and described above.

In a further alternative embodiment illustrated cross-sectionally in FIGS. 4A–4C, an implant structure 92 (FIG. 4C) of increased strength and durability is illustrated. All of the structures, components, materials, dimensions, and processes used in connection with implant structure 92 are the same as those associated with implant structure 10 unless otherwise indicated. The implant structure 92 is designed for use in high-stress environments where enhanced strength is an important factor. With reference to FIGS. 4A–4B, a key difference between implant structure 10 and implant structure 92 involves the use of primary and secondary containment members 94, 96. Specifically, primary containment member 94 is substantially identical to containment member 12 in structure, function, size, and other parameters. Accordingly, unless otherwise stated herein, all of the information provided above regarding containment member 12 is equally applicable to primary containment member 94. Regarding construction materials, the primary containment member 94 can be manufactured from the collagen materials described above including collagen foam or non-cellular sheets of collagen. Alternatively, the primary containment member 94 may be made from other materials including but not limited to silicone rubber, plastic, and the like. As illustrated in FIG. 4A, primary containment member 94 specifically includes an open top portion 98 and a closed bottom portion 100. In addition, the primary containment member 94 further includes a continuous tubular side wall 102, and an internal cavity 104 therein surrounded by the side wall 102. Regarding the secondary containment member 96, all of the information provided above involving containment member 12 is equally applicable to secondary containment member 96 unless otherwise stated herein. Specifically, the secondary containment member 96 includes an open top portion 108 and a closed bottom portion 110. In addition, the secondary containment member 96 further includes a continuous tubular side wall 112, and an internal cavity 114 therein surrounded by the side wall 112. Secondary containment member 96 is substantially identical to primary containment member 94 regarding the parameters described above, except that the secondary containment member 96 is about 1–10% larger in size and volumetric capacity compared with the primary containment member 94. Specifically, the dimensions of the secondary containment member 96 and internal cavity 114 therein are larger than the corresponding dimensions of the primary containment member 94 and its internal cavity 104 by the foregoing percentage. Also, it is preferred that the secondary containment member 96 be manufactured from collagen materials including collagen foam or non-cellular sheets of collagen as described above. Secondary containment member 96 is sized to receive primary containment member 94 entirely therein in a nested arrangement as illustrated cross-sectionally in FIG. 4B.

Prior to nesting of the primary containment member 94 within the secondary containment member 96, an optional portion or layer of reinforcement material 120 may be wrapped around the exterior surface 122 of the primary containment member 94 or otherwise positioned between the primary and secondary containment members 94, 96. If desired, the layer of reinforcement material 120 may be adhesively affixed to the exterior surface 122 of the primary containment member 94 using conventional adhesive compositions applied to the containment member 94, the layer of reinforcement material 120, or both. Exemplary adhesive compositions suitable for this purpose include but are not limited to autologous fibrin glue, cyanoacrylate adhesives, silicone rubber cement and the like. Alternatively, the layer of reinforcement material 120 may be placed within the secondary containment member 96 and positioned against the inner surface 124 thereof. Adhesive compositions of the same type listed above regarding attachment of the layer of reinforcement material 120 to the primary containment member 94 may optionally be used to secure the layer of reinforcement material 120 within the secondary containment member 96.

Many different materials may be used to construct the layer of reinforcement material 120, and the present invention shall not be limited to any particular compositions for this purpose. In a preferred embodiment, silicone rubber, polytetrafluoroethylene (e.g. Teflon®), biocompatible plastics known in the art which are conventionally used for medical applications, or a selected metal (e.g. titanium) may be used in sheet or mesh form as the layer of reinforcement material 120. If used in mesh form, the layer of reinforcement material 120 will optimally have the same dimensional and physical characteristics as the portion of mesh 88 described above. The layer of reinforcement material 120 may cover all or part of the primary containment member 94 as desired. Also, in a preferred embodiment, the layer of reinforcement material 120 will have an average, optimal thickness of about 1/64–1/8 in.

As illustrated in FIG. 4C, the completed implant structure 92 has the primary containment member 94 completely nested (e.g. positioned) within the internal cavity 114 of the secondary containment member 96, with the layer of reinforcement material 120 being positioned and maintained between the primary and secondary containment members 94, 96. FIG. 4C also illustrates the presence of a solid mass 125 positioned within the internal cavity 104 of the primary containment member 94 which is formed from the granular implant composition 40 and activator material 50. In particular, the implant composition 40 and activator material 50 combine to produce the pliable mixture 51 described above in the embodiment of FIGS. 1A–1E and illustrated in FIG. 4B. The solid mass 125 may likewise include one or more optional reinforcement members (not shown) of the same type indicated above regarding reinforcement members 82. To maintain the pliable mixture 51 (and solid mass 125) in position within the implant structure 92, a first cap member 126 and a second cap member 127 are provided and respectively secured to the primary and secondary containment members 94, 96 as illustrated in FIGS. 4B and 4C. Specifically, the first cap member 126 is secured to the rim 128 on the open top portion 98 of the primary containment member 94, with the second cap member 127 being secured to the rim 129 on the open top portion 108 of the secondary containment member 96. As illustrated, the first cap member 126 is smaller than the second cap member 127 and particularly sized for placement on the primary containment member 94. In contrast, the second cap member 127 is sized for attachment to the secondary containment member 96 and is designed to cover the primary containment member 94 (and first cap member 126) so that these components are completely retained within the secondary containment member 96. Aside from differences in size as described above, the first and second cap members 126, 127 are substantially identical to the cap member 89 in terms of construction material, configuration, and functional capabilities. Furthermore, the first and second cap members 126, 127 are respectively attached to the primary and secondary containment members 94, 96 in the same manner used to attach the cap member 89 to the open top portion 14 of the containment member 12 as previously described.

The primary and secondary containment members 94, 96 may be secured together within the implant structure 92 using many different methods and materials. For example, after assembly of the implant structure 92 (and prior to placement of the implant composition 40 and activator material 50 within the internal cavity 104 of the primary containment member 94), the containment members 94, 96 may be stapled or sutured together using conventional systems known in the art for this purpose. Alternatively, adhesive compositions (e.g. autologous fibrin glue, cyanoacrylate adhesives, silicone rubber cement, and the like) may be applied to the primary containment member 94, the secondary containment member 96, or both prior to assembly of the implant structure 92. Other procedures and materials associated with the implant structure 92 (including the type, amount, and character of the implant composition 40 and activator material 50 to be used within the internal cavity 104 of the primary containment member 94) are substantially identical to those listed above regarding implant structure 10. Also, as previously noted, the implant structure 92 may include a plurality of reinforcement members therein (not shown) of the same type described above regarding reinforcement members 82. While the remaining descriptive information provided below shall be presented with reference to implant structure 10, it is equally applicable to implant structure 92 unless otherwise stated.

Referring back to FIGS. 1A–1E, after combining the granules 44 of implant composition 40 with the selected activator material 50 (and insertion of the reinforcement member or members 82 if desired), the pliable mixture 51 will form an agglomerated solid mass 130 (FIG. 1E), thereby causing solidification of the entire containment member 12. As described below, formation of the solid mass 130 occurs after combination of the granules 44 with the activator material 50 and after the implant structure 10 is surgically inserted within a patient and physically configured (e.g. manually shaped) by the treating physician. The solid mass 130 has a rigid character which functionally resembles natural bone. This rigidity enables the completed implant structure 10 to be used for numerous constructive, space-filling, and reconstructive purposes as described above. Setting time of the activator material 50 in order to prepare the solid mass 130 will vary in view of the specific compositions being used for this purpose, as well as the particle size and amount of the selected implant composition 40 which is placed within the containment member 12. Use of the activator materials 50 described herein results in a setting time which is sufficiently long to enable a treating physician to properly position the implant structure 10 within a patient and physically manipulate its shape to conform with adjacent tissue materials. Regarding the adhesive-type activator materials 50 listed above (as well as other equivalent adhesive compositions suitable for use herein) an average setting time will be about 1.0–60 minutes, depending on the size of the implant structure 10, its shape, the particle size of the implant composition being used, the chemical character of the selected activator (adhesive) material 50, and other extrinsic factors. When hydroxyapatite cement materials are used which preferably involve the addition of sterile water or saline solutions instead of adhesives, normal setting times will be about 10–30 minutes. Exact setting times in all embodiments can be determined in accordance with preliminary pilot experiments on the materials and components being used for any given situation.

Figure 2:
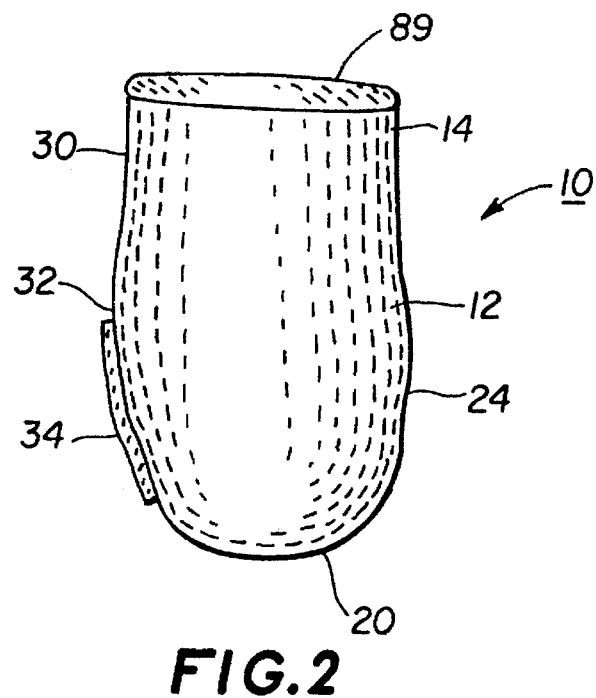
FIG. 2 is an enlarged schematic side view of an exemplary completed medical implant structure produced in accordance with a preferred embodiment of the invention as illustrated in FIGS. 1A–1E.
Figure 3:
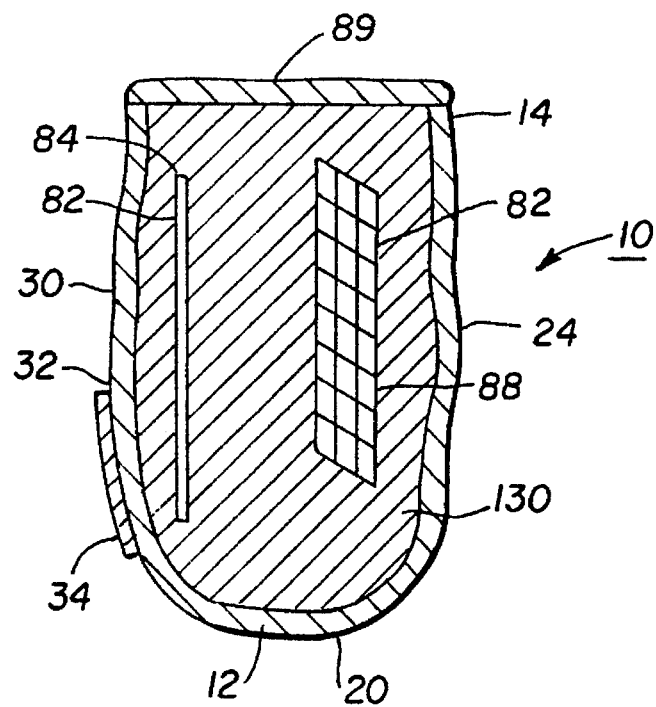
FIG. 3 is a partial, cross-sectional enlarged schematic view of the medical implant structure of FIG. 2 illustrating the components and compositions therein.

The completed implant structure 10 is illustrated in FIGS. 1E, 2, and 3. In particular, the cross-sectional view of FIG. 3 shows the various components of the implant structure 10 including containment member 12, the solid mass 130 within the containment member 12 formed from the activator material 50 and implant composition 40, the reinforcement members 82, and the cap member 89. Further information regarding the implant structure 10 including its functional capabilities will be presented below.

While the process described above and illustrated in FIGS. 1A–1E represents a preferred production method regarding the implant structure 10, an alternative production method is schematically illustrated in FIGS. 5A–5F. With reference to FIGS. 5A–5F, the production method illustrated therein is substantially identical to the method described above regarding FIGS. 1A–1E except as indicated below. Specifically, the method of FIGS. 5A–5F involves a different technique for delivering the liquid activator material 50 into the implant composition 40.

With continued reference to FIGS. 5B–5C, prior to addition of the activator material 50, a tubular rod member 150 is provided which is optimally manufactured of a rigid, inert material (e.g. polycarbonate plastic, silicone rubber, aluminum, titanium, ceramic, stainless steel, glass, and the like). The size (e.g. length and width) of the rod member 150 will necessarily vary in view of many factors, including the size of the implant structure 10 to be manufactured. As a general rule, the rod member 150 should be at least as long as the containment member 12 with which it is used, and longer if desired. The rod member 150 will also have an optimum diameter of about $\frac{1}{32}$–$\frac{1}{4}$ in. with an upper end 152 and a lower end 154. In addition, the rod member 150 will have an internal, elongate bore 156 which passes entirely through the rod member 150. The bore 156 preferably has a uniform internal diameter which is constant from the upper end 152 of the rod member 150 to the lower end 154 thereof. The internal diameter of the bore 156 will preferably be larger than the diameter of any needle or comparable delivery unit used to deliver the selected liquid activator material 50 into the containment member 12 (e.g. needle 72 associated with dual syringe unit 54). In a preferred embodiment involving the use of conventional and standard needles/fluid delivery systems, the bore 156 within the rod member 150 will have an internal diameter of about 1/64–15/16 in. with a volumetric capacity of about 0.1–4.0 ml. However, the present invention shall not be limited to any particular dimensions regarding the rod member 150 and/or bore 156.

While the embodiment of FIGS. 5A–5F will be discussed with reference to autologous fibrin glue as the activator material 50 which is delivered using dual syringe unit 54, the embodiment of FIGS. 5A–5F shall not limited to any particular activator material 50 or delivery system. Immediately prior to addition of the liquid activator material 50 into the granules 44 of the implant composition 40, the rod member 150 is inserted into and through the implant composition 40 (FIG. 5C). In a preferred embodiment, the rod member 150 is inserted so that the lower end 154 thereof is immediately adjacent the closed bottom portion 20 (FIG. 5C) of the containment member 12. Due to the relatively small internal diameter of the bore 156 through the rod member 150 and the particular physical character of the above-listed implant compositions 40, only a small portion (if any) of the granules 44 will normally enter the bore 156 of the rod member 150 during insertion within the containment member 12 as described above. As a result, the bore 156 will remain substantially open so that the liquid activator material 50 may be received therein.

At this point, the activator material 50 may now be added to the implant composition 40 to form pliable mixture 51 (FIG. 5E). As illustrated in FIGS. 5A–5F which show the use of autologous fibrin glue 78 as the activator material 50, this would involve insertion of the lower section 76 of the needle 72 partially within the bore 156 through the upper end 152 of the rod member 150, followed by activation of the dual syringe unit 54 as described above in order to deliver autologous fibrin glue 78 into the bore 156. Other liquid activator materials 50 and fluid delivery systems may be used in the same manner regarding bore 156 and rod member 150. Accordingly, this embodiment of the invention shall not be limited exclusively to the delivery of autologous fibrin glue 78 or the use of needle 72 as noted above.

After addition of the liquid activator material 50 to the bore 156 in the rod 150, the activator material 50 will either immediately drain into the implant composition 40 or collect within the bore 156 and drain gradually into the implant composition 40 to form the pliable mixture 51. Drainage rates associated with the activator material 50 will depend on a variety of factors including the particle size of the granules 44 associated with the selected implant composition 40, as well as the amount of liquid activator material 50 being added. The rod member 150 is then removed from the implant composition 40. In situations where the liquid activator material 50 does not drain immediately and collects within the bore 156, remaining amounts of the activator material 50 within the bore 156 will drain into and through the granules 44 in a continuous, uniform manner from the lower end 154 of the rod member 150 as it is removed. During removal of the rod member 150 in this manner, the liquid activator material 50 will be gradually dispensed from the bore 156 in a uniform manner through the lower end 154 of the rod member 150 as it passes upwardly through the implant composition 40.

Regardless of the drainage time associated with the activator material 50, the delivery system of FIGS. 5A–5F minimizes and effectively reduces the amount of physical agitation necessary to achieve proper mixing of the activator material 50 and granular implant composition 40. Once the activator material 50 is supplied to the implant composition 40 in the foregoing manner, it is able to laterally diffuse into surrounding regions of the composition 40 at a rapid, consistent, and uniform rate. In this regard, use of the foregoing system ensures that the activator material 50 is delivered to all portions of the implant composition 40, including those adjacent the closed bottom portion 20 of the containment member 12. The remaining steps in the process of FIGS. 5A–5F are substantially identical to those described above regarding the embodiment of FIGS. 1A–1E, including the addition of one or more reinforcement members 82 which will preferably occur prior to or simultaneously with introduction of the rod member 150 into the containment member 12.

As noted above in the process of FIGS. 5A–5F, the activator material 50 is added to the bore 156 of the rod member 150 after the rod member 150 is positioned within the implant composition 40. Alternatively, the activator material 50 may be added to the bore 156 of the rod member 150 during removal of the rod member 150 from the composition 40. As a result, the activator material 50 will be continuously added to the bore 156 and delivered from the lower end 154 of the rod member 150 as it is being pulled out of the implant composition 40. Under certain circumstances as determined by preliminary pilot studies, this alternative approach may result in more thorough mixing of the activator material 50 and granules 44 of the implant composition 40. This approach may also be useful when the amount of activator material 50 to be used exceeds the volumetric capacity of the bore 156 in the rod member 150, thereby preventing all of the activator material 50 from being added to the bore 156 in a single quantity. However, it should be noted that both of the approaches described above in connection with FIGS. 5A–5F shall be deemed equivalent to each other in function, result, and inventive character.

In a further variation of the foregoing procedure, the rod member 150 may be allowed to remain within the implant composition 40 in the containment member 12 after the activator material 50 has been delivered in order to provide the completed implant structure 10 with additional internal support. If the rod member 150 is to remain within the containment member 12, it is preferred that it have a length which does not exceed that of the containment member 12 and be constructed of a material which is bendable during placement of the implant structure 10 within a patient. An exemplary material suitable for this purpose would involve silicone rubber or a selected biocompatible plastic as noted above.

Figure 6:
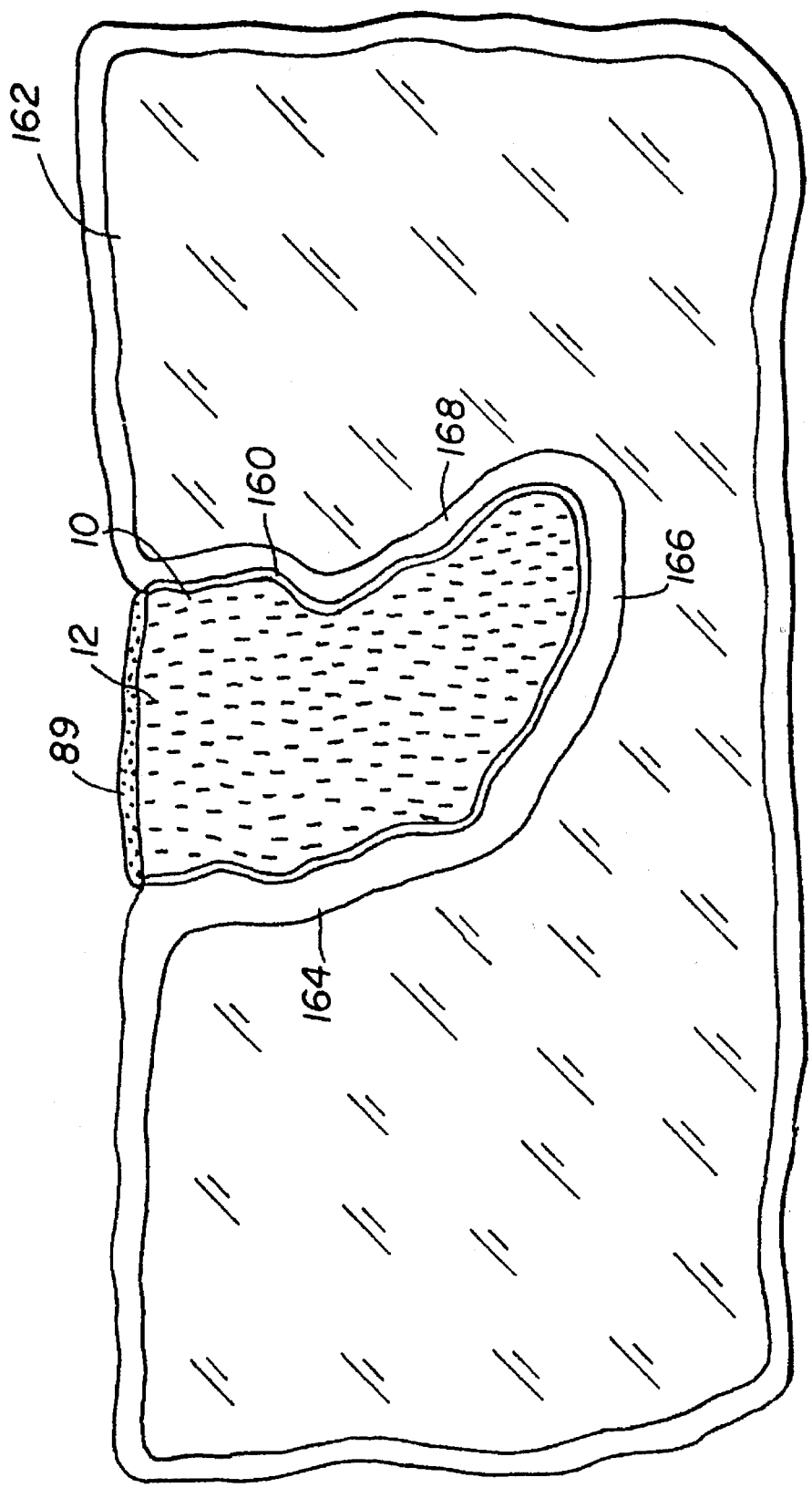
FIG. 6 is a schematic illustration of the medical implant structure of FIG. 2 which has been surgically inserted and appropriately configured/shaped by the treating physician so that it resides adjacent to and against selected tissue materials in a conforming manner.

With reference to FIG. 6, an implant structure 10 produced in accordance with the present invention is illustrated after surgical insertion within a patient. The term "patient" and "living subject" as used herein shall primarily encompass human subjects, although the implant structure 10 may also be configured for use in veterinary or experimental procedures associated with animals. As illustrated in FIG. 6, the implant structure 10 is shown in position within a cavity 160 in tissue region 162 surrounded by tissue portions 164, 166, 168. The tissue portions 164, 166, 168 many consist of bony and/or soft tissues. For example, the tissue portions 164, 166, 168 may involve structures ranging from sections of the external ear canal to portions of a patient's jaw bone or cranial skull base. In this regard, the present invention shall not be limited to use in connection with any particular types of tissue materials or anatomical regions.

Immediately after placement of the implant structure 10 within the cavity 160 in tissue region 162 as shown in FIG. 6, the structure 10 (e.g. the containment member 12) is physically manipulated (e.g. manually molded/shaped) by the physician so that it dimensionally conforms with the tissue region 162. The term "dimensionally conform" as used herein shall signify a situation wherein the shape of the implant structure 10 corresponds with (e.g. matches) the contours of the tissue region 162 so that the implant structure 10 can precisely engage the tissue region 162 within cavity 160 as illustrated in FIG. 6. Conforming engagement of the implant structure 10 within the cavity 160 ensures that the structure 10 does not extend outwardly from the tissue region 162 in an undesirable manner where it is not needed or desired. This is especially important in ear surgery where it is essential not to block or otherwise interfere with surrounding tissue regions, cavities, or passageways. This factor is equally important in cosmetic/reconstructive surgery (e.g. jaw reconstruction and the like) in order to ensure that a desired aesthetic appearance is maintained in the patient. Conforming engagement of the implant structure 10 within the cavity 160 also avoids the formation of gaps therebetween which ensures that the implant structure 10 will provide a maximum degree of structural support.

The use of collagen materials (e.g. foam-type or non-cellular collagen) for the containment member 12 and cap member 89 ultimately enables a significant degree of physical and biological integration (e.g. joining) of these components to the tissue portions 164, 166, 168. This process occurs in view of the unique structural and functional characteristics of the implant structure 10, and ensures long-term or permanent placement of the implant structure 10 in its designated position. Physical (e.g. shape) integration between the implant structure 10 and surrounding tissues is basically defined to involve dimensional conformation and solidification of the implant structure 10 within the selected tissue area or region. Physical integration normally occurs in a rapid manner upon manipulation of the implant structure 10 by the treating physician so that it dimensionally conforms with the tissue regions of concern. After dimensional conformation, the implant structure 10 will solidify within the time parameters listed above (which provide a sufficient delay period to permit proper physical manipulation of the implant structure 10 by the physician before solidification occurs). Precise dimensional conformation of the implant structure 10 as described herein prevents undesired axial, lateral, or rotational movement of the implant structure 10 since it will be tightly engaged against and/or within desired tissue regions. Biological integration of the implant structure 10 and surrounding tissues normally occurs over a period of about 6–18 weeks following implantation. Biological integration is a different process from physical integration, and involves the unique character of the collagen materials used to produce the implant structure 10. Specifically, soft or bony tissue cells positioned adjacent to and in contact with the collagen materials used to form the containment member 12 grow into the collagen materials in order to form an integrated collagen/cell matrix. As a result, the implant structure 10 eventually becomes biologically integrated with the foregoing tissue materials, thereby fixing it securely in position at its desired location and allowing it to function as an integral support structure within the patient. Furthermore, after the foregoing integration process occurs regarding the collagen materials, additional tissue integration will often take place with the materials inside the containment member 12. For example, in a process known as "osteoconduction", bone materials outside of the containment member 12 which integrate with the collagen materials described above will likewise grow onto the surface of the solidified matrix inside the containment member 12, depending on its chemical characteristics. Osteoconduction will typically occur in connection with the exemplary materials listed above for use as the implant composition 40. As a result of osteoconduction, the implant structure 10 will be fixedly and rigidly integrated in position.

It should also be noted that use of the non-stick coating material 34 applied to the containment member 12 will prevent the biological integration process from occurring where the non-stick coating material 34 contacts the tissue materials of concern. Prevention is accomplished because the non-stick coating material 34 forms an inert barrier between the collagen compositions used to construct the containment member 12 and adjacent tissue materials. As a general rule, prevention of the biological integration process is appropriate in certain cases where it is not anatomically necessary or physiologically imperative to have the implant structure 10 bound to all portions of adjacent tissue materials. In fact, it may be undesirable or inappropriate to have the implant structure 10 bound to certain tissue zones which need to move during use. This situation arises in many medical environments. For example, in reconstructive ear surgery involving the production of a new stapes piston using the implant technology described herein, it is important that various portions of the piston be free to move relative to surrounding tissues and other structures. Accordingly, the decision to use a non-stick coating material 34 as described herein will depend on a wide variety of circumstances, including but not limited to the physical environment for which the implant structure 10 is intended and the exact type of implant structure 10 being produced.

Finally, it is important to note that, if desired or appropriate as determined by the treating physician, multiple implant structures 10 may be positioned adjacent each other in a "building block" arrangement within a tissue cavity to provide an additional degree of structural support and space-filling capacity. Accordingly, the present invention shall not be limited to the use of a single implant structure 10 within a patient.

The present invention represents a highly efficient implant structure which is readily manufactured. Upon insertion within a patient, it provides a considerable degree of structural support. In addition, it is readily shaped (e.g. configured) by the treating physician to ensure conformity of the implant structure with adjacent tissue materials. The components used to produce the implant structure are biocompatible, thereby enabling the structure to be used in an effective manner without adverse side effects. The present invention therefore represents an advance in the art of medical implant technology.

Having herein described preferred embodiments of the present invention, it is anticipated that suitable modifications may be made thereto by individuals skilled in the relevant art which nonetheless remain within the scope of the invention. For example, the invention shall not be limited regarding the physiological environment in which it is used, the dimensions of implant structures produced in accordance with the invention, and other parameters associated therewith.

Accordingly, the present invention shall only be construed in connection with the following claims:

The invention that is claimed is:

1. A medical implant structure comprising:

a containment member comprising an open top portion, a closed bottom portion, a side wall, and an internal cavity therein surrounded by said side wall, said containment member being comprised of collagen;

a supply of a granular implant composition positioned within said internal cavity of said containment member, said implant composition being comprised of a plurality of individual granules; and a supply of an activator material positioned within said internal cavity of said containment member in combination with said implant composition, said activator material adhering said individual granules of said implant composition together to form a temporarily pliable mixture which ultimately solidifies to produce a solid mass sufficiently rigid for use within said implant structure.

2. The implant structure of claim 1 further comprising a cap member secured to said top portion of said containment member to maintain said mixture within said containment member.

3. The implant structure of claim 2 wherein said cap member is comprised of collagen.

4. The implant structure of claim 1 wherein said activator material is selected from the group consisting of autologous fibrin glue, cyanoacrylate glue, silicone rubber cement, water, and saline solution.

5. The implant structure of claim 1 wherein said granular implant composition is selected from the group consisting of hydroxyapatite, powdered hydroxyapatite cement, natural bone, and a bioceramic composition.

6. A medical implant structure comprising:

a containment member comprising an open top portion, a closed bottom portion, a side wall, and an internal cavity therein surrounded by said side wall, said containment member being comprised of collagen;

a supply of a granular implant composition positioned within said internal cavity of said containment member, said implant composition being comprised of a plurality of individual granules;

a supply of an activator material positioned within said internal cavity of said containment member in combination with said implant composition, said activator material adhering said individual granules of said implant composition together to form a temporarily pliable mixture which ultimately solidifies to produce a solid mass sufficiently rigid for use within said implant structure; and at least one elongate reinforcement member imbedded within said implant composition, said reinforcement member providing said implant structure with additional structural support.

7. The implant structure of claim 6 wherein said elongate reinforcement member is comprised of a metal selected from the group consisting of titanium and stainless steel.

8. The implant structure of claim 6 further comprising a cap member secured to said top portion of said containment member to maintain said mixture and said reinforcement member within said containment member.

9. The implant structure of claim 8 wherein said cap member is comprised of collagen.

10. The implant structure of claim 6 wherein said activator material is selected from the group consisting of autologous fibrin glue, cyanoacrylate glue, silicone rubber cement, water, and saline solution.

11. The implant structure of claim 6 wherein said granular implant composition is selected from the group consisting of hydroxyapatite, powdered hydroxyapatite cement, natural bone, and a bioceramic composition.

12. A medical implant structure comprising:

a primary containment member comprising an open top portion, a closed bottom portion, a side wall, and an internal cavity therein;

a secondary containment member comprising an open top portion, a closed bottom portion, a side wall, and an internal cavity therein, said secondary containment member being comprised of collagen, said primary containment member being positioned within said internal cavity of said secondary containment member so that said primary containment member is nested within said secondary containment member;

a supply of a granular implant composition positioned within said internal cavity of said primary containment member; and a supply of an activator material positioned within said internal cavity of said primary containment member in combination with said implant composition, said activator material and said implant composition forming a pliable mixture which ultimately solidifies to produce a solid mass sufficiently rigid for use within said implant structure.

13. The implant structure of claim 12 further comprising at least one elongate reinforcement member imbedded within implant composition, said reinforcement member providing said implant structure with additional structural support.

14. The implant structure of claim 12 further comprising a first cap member secured to said top portion of said primary containment member to maintain said mixture within said primary containment member, and a second cap member secured to said top portion of said secondary containment member to maintain said primary containment member within said secondary containment member.

15. A medical implant structure comprising:

a primary containment member comprising an open top portion, a closed bottom portion, a side wall, and an internal cavity therein;

a secondary containment member comprising an open top portion, a closed bottom portion, a side wall, and an internal cavity therein, said secondary containment member being comprised of collagen, said primary containment member being positioned within said internal cavity of said secondary containment member so that said primary containment member is nested within said secondary containment member;

a layer of reinforcement material positioned between said primary containment member and said secondary containment member, said layer of reinforcement material providing said implant structure with additional structural support;

a supply of a granular implant composition positioned within said internal cavity of said primary containment member; and a supply of an activator material positioned within said internal cavity of said primary containment member in combination with said implant composition, said activator material and said implant composition forming a pliable mixture which ultimately solidifies to produce a solid mass sufficiently rigid for use within said implant structure.

16. The implant structure of claim 15 further comprising at least one elongate reinforcement member imbedded within implant composition, said reinforcement member providing said implant structure with additional structural support.

17. A method for structurally reinforcing a tissue region within a living subject comprising the steps of:
providing a medical implant structure comprising:
a containment member comprising an open top portion, a closed bottom portion, a side wall, and an internal cavity therein surrounded by said side wall, said containment member being comprised of collagen;
a supply of a granular implant composition positioned within said internal cavity of said containment member, said implant composition being comprised of a plurality of individual granules; and
a supply of an activator material positioned within said internal cavity of said containment member in combination with said implant composition, said activator material adhering said individual granules of said implant composition together to form a temporarily pliable mixture which ultimately solidifies to produce a solid mass sufficiently rigid for use within said implant structure;
inserting said implant structure within said living subject prior to solidification of said mixture;
positioning said implant structure adjacent to and against said tissue region to be reinforced; and
physically manipulating and shaping said implant structure prior to solidification of said mixture so that said implant structure dimensionally conforms with said tissue region.

18. A method for structurally reinforcing a tissue region within a living subject comprising the steps of:
providing a containment member comprising an open top portion, a closed bottom portion, a side wall, and an internal cavity therein surrounded by said side wall, said containment member being comprised of collagen;
providing a supply of a granular implant composition, said implant composition being comprised of a plurality of individual granules;
filling said internal cavity of said containment member with said implant composition;
combining said implant composition with an activator material to produce a medical implant structure from said containment member, said activator material adhering said individual granules of said implant composition together to form a temporarily pliable mixture which ultimately solidifies to produce a solid mass sufficiently rigid for use within said implant structure;
inserting said implant structure within said living subject prior to solidification of said mixture;
positioning said implant structure adjacent to and against said tissue region to be reinforced; and
physically manipulating and shaping said implant structure prior to solidification of said mixture so that said implant structure dimensionally conforms with said tissue region.

19. A medical implant structure comprising:
a containment member comprising an open top portion, a closed bottom portion, a side wall, and an internal cavity therein surrounded by said side wall, said side wall comprising an exterior surface, with at least one section of said exterior surface comprising a portion of non-stick coating material applied thereto, said containment member being comprised of collagen;
a supply of a granular implant composition positioned within said internal cavity of said containment member, said implant composition being comprised of a plurality of individual granules; and
a supply of an activator material positioned within said internal cavity of said containment member in combination with said implant composition, said activator material adhering said individual granules of said implant composition together to form a temporarily pliable mixture which ultimately solidifies to produce a solid mass sufficiently rigid for use within said implant structure.

20. A medical implant structure comprising:
a containment member comprising an open top portion, a closed bottom portion, a side wall, and an internal cavity therein surrounded by said side wall, said side wall comprising an exterior surface, with at least one section of said exterior surface comprising a portion of non-stick coating material applied thereto, said containment member being comprised of collagen;
a supply of a granular implant composition positioned within said internal cavity of said containment member, said implant composition being comprised of a plurality of individual granules;
a supply of an activator material positioned within said internal cavity of said containment member in combination with said implant composition, said activator material adhering said individual granules of said implant composition together to form a temporarily pliable mixture which ultimately solidifies to produce a solid mass sufficiently rigid for use within said implant structure; and
at least one elongate reinforcement member imbedded within said implant composition, said reinforcement member providing said implant structure with additional structural support.

21. A method for structurally reinforcing a tissue region within a living subject comprising the steps of:
providing a containment member comprising an open top portion, a closed bottom portion, a side wall, and an internal cavity therein surrounded by said side wall, said containment member being comprised of collagen;
providing a supply of a granular implant composition, said implant composition being comprised of a plurality of individual granules;
filling said internal cavity of said containment member with said implant composition;
inserting a rod member within said implant composition in said containment member, said rod member comprising an upper end, a lower end, and an elongate bore passing through said rod member from said upper end to said lower end;
supplying said bore with an activator material so that said activator material can pass into said implant composition from said bore to produce a medical implant structure from said containment member, said activator material adhering said individual granules of said implant composition together to form a temporarily pliable mixture which ultimately solidifies to produce a solid mass sufficiently rigid for use within said implant structure;
inserting said implant structure within said living subject prior to solidification of said mixture;
positioning said implant structure adjacent to and against said tissue region to be reinforced; and physically manipulating and shaping said implant structure prior to solidification of said mixture so that said implant structure dimensionally conforms with said tissue region.

22. A method for structurally reinforcing a tissue region within a living subject comprising the steps of:

providing a containment member comprising an open top portion, a closed bottom portion, a side wall, and an internal cavity therein surrounded by said side wall, said containment member being comprised of collagen;

providing a supply of a granular implant composition, said implant composition being comprised of a plurality of individual granules;

filling said internal cavity of said containment member with said implant composition;

positioning at least one elongate reinforcement member within said implant composition in said containment member;

inserting a rod member within said implant composition in said containment member, said rod member comprising an upper end, a lower end, and an elongate bore passing through said rod member from said upper end to said lower end;

supplying said bore with an activator material so that said activator material can pass into said implant composition from said bore to produce a medical implant structure from said containment member, said activator material adhering said individual granules of said implant composition together to form a temporarily pliable mixture which ultimately solidifies to produce a solid mass sufficiently rigid for use within said implant structure;

inserting said implant structure within said living subject prior to solidification of said mixture;

positioning said implant structure adjacent to and against said tissue region to be reinforced; and physically manipulating and shaping said implant structure prior to solidification of said mixture so that said implant structure dimensionally conforms with said tissue region.

23. A medical implant structure comprising:

a containment member comprising an open top portion, a closed bottom portion, a side wall, and an internal cavity therein surrounded by said side wall, said containment member being comprised of multicellular collagen foam;

a supply of a granular implant composition positioned within said internal cavity of said containment member, said implant composition being comprised of a plurality of individual granules; and a supply of an activator material positioned within said internal cavity of said containment member in combination with said implant composition, said activator material adhering said individual granules of said implant composition together to form a temporarily pliable mixture which ultimately solidifies to produce a solid mass sufficiently rigid for use within said implant structure.

* * * * *